United States Patent [19]

Thrower

[11] Patent Number: 4,759,355
[45] Date of Patent: Jul. 26, 1988

[54] MALE UNDERGARMENT

[76] Inventor: John H. Thrower, 1231 Belrose La., Charlotte, N.C. 28209

[21] Appl. No.: 34,379

[22] Filed: Apr. 6, 1987

[51] Int. Cl.$^4$ .............................. A61F 5/40; A41B 9/02
[52] U.S. Cl. .......................................... 128/159; 2/405
[58] Field of Search ..................... 2/405, 403; 128/159, 128/160, 158, 157

[56] References Cited

U.S. PATENT DOCUMENTS 2,328,953  9/1943  Chatfield et al. ..................... 128/159
2,736,036  2/1956  Sinigagliesi ............................. 2/405
2,872,685  2/1959  Denbo ............................. 128/159 X

FOREIGN PATENT DOCUMENTS 2258805  8/1975  France ..................................... 2/405

Primary Examiner—H. Hampton Hunter

[57] ABSTRACT

A male undergarment formed from a tubular body portion having a scrotum-underlying section with an opening defined therein and an outer genitalia-concealing panel connected to the crotch section of the tubular body portion and extending along the leg openings and up to the waistband, thereby forming a pocket with the front area of the tubular body portion along the waistband. The defined opening receives the complete genitalia to be encased by the pocket.

14 Claims, 2 Drawing Sheets

MALE UNDERGARMENT

BACKGROUND OF THE INVENTION

This invention relates to wearing apparel and more particularly to a male undergarment generally referred to as a brief which gives the comfort of a snug fit yet permits free movement of the portions of the body adjacent thereto. For many years, there have been relatively few undergarment configurations developed which strive to provide the wearer with a greater degree of comfort and accessibility than that normally experienced in conventional garments. Examples of such configurations are undergarments which are intended to provide support when the wearer is in a sitting position, flap coverings over penis openings, and those undergarments intended for use by men suffering from various ailments such as kidney, bowel, bladder, or prostrate disorders. The garments developed in the past have attempted to provide relief to the wearer in the area of health protection; however, they have not adequately provided means for gently supporting the genitals while simultaneously separating and encasing the adjacent skin surfaces and providing a layer of fabric as an aid to perspiration control, thereby protecting the wearer from the effects of the disorders of heat rash and/or herpes or the reduced sperm count which is experienced by some 30% of males as a result of increased scrotal temperature caused by the average snug brief compressing the scrotal sac so close to the body.

Some prior art undergarments have attempted to solve the health-related problem concerning proper air circulation to the genitals of the wearer; however, the majority, for the most part, inhibit air circulation.

BRIEF SUMMARY OF THE INVENTION

In its basic form, the present invention includes a tubular body portion having front, back, and crotch areas and a pair of leg-receiving openings with the front area in which a defined opening receives the complete male genitals. The waistband is secured to the upper edge of the tubular body portion, and an outer genital-covering panel is secured at one end to the crotch of the tubular body porton and then extends upwardly along the leg openings to the sides and then upwardly therefrom to the waistband, thus forming a pocket between the front panel and the outer covering panel. The upper edge of the outer genital-covering panel is trimmed with a stretchable element that will retain that edge against the waistband in a normal condition but will stretch out and down to disclose a pocket between the front area of the tubular body portion and the genital-covering panel when it is displaced downwardly and away from the waistband by the wearer.

OBJECTIVES OF THE INVENTION

Essentially it is the primary object of this invention to provide a male undergarment having a construction that will support separately the male genitals, provide a high degree of comfort to the wearer, and provide protection to the body area covered by the garment by preventing excess heat and the excess perspiration easily experienced in this area of the body.

It is another objective of the present invention to provide a male undergarment which both covers and supports a wearer's genitals while allowing air circulation thereto.

It is yet another objective of the present invention to provide an undergarment which simultaneously provides health protection, support, comfort, and privacy without a radical departure from the customary appearance of a brief.

Yet still another objective of the present invention is to provide a genital-receiving pocket between two contiguous panels which is accessible through an opening lying along and adjacent the waistband.

Yet another objective of the present invention is to provide a male undergarment in a variety of sizes and styles adaptable to fit differently sized wearers which is easy to don and remove, will provide a high degree of comfort for the male genitals and will allow maximum free body movement, the brief being simple in construction and requiring a minimum number of stitching operations during fabrication. It is particularly effective and comfortable in the bikini style having the upper border in the area of the hip, but is also readily adaptable to the more full-cut style of the waist-high brief.

These, together with other objectives and advantages, will become more apparent after consideration of the following detailed description of the present invention taken in conjunction with the accompanying drawings wherein like characters of reference designate like parts throughout the several views.

DETAILED DESCRIPTION OF THE INVENTION

Figure 1:
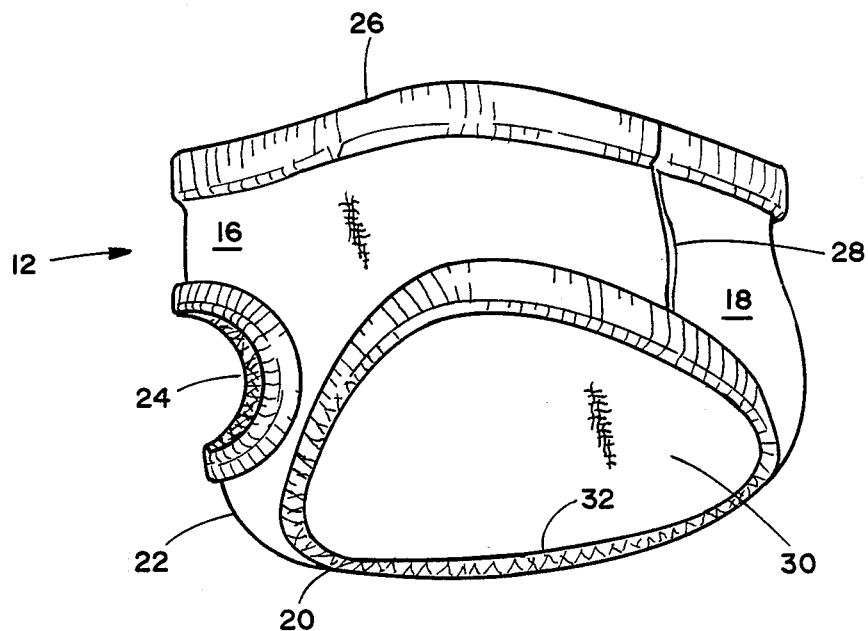
FIG. 1 is a side elevational view of the tubular body portion of the present invention illustrating the genital-receiving opening, waistband, and one of the two leg bands.
Figure 2:
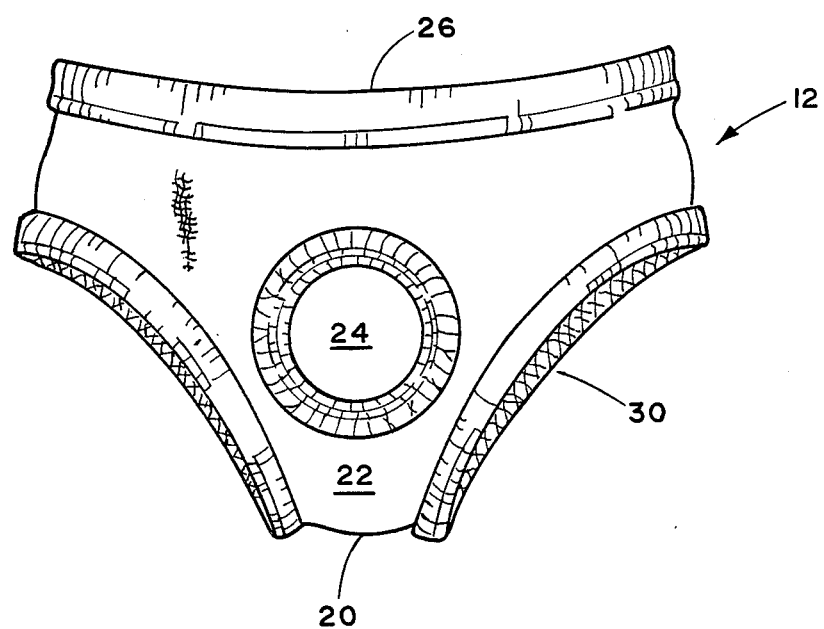
FIG. 2 is a front elevational view of the tubular portion shown in FIG. 1 illustrating both leg bands, one encircling each of the leg openings of the tubular body portion.
Figure 3:
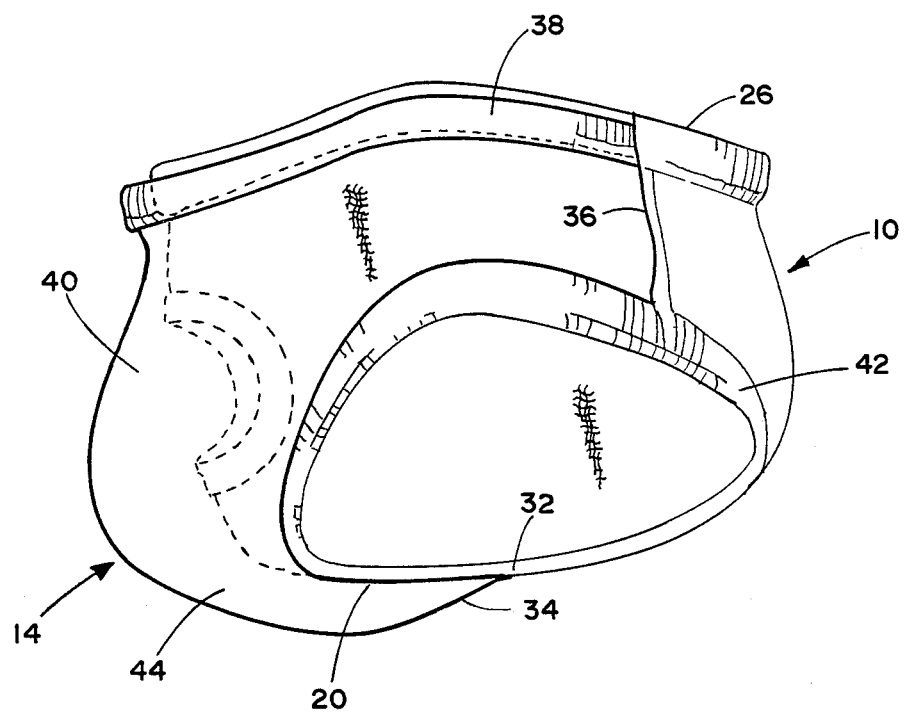
FIG. 3 is a side elevational view of the tubular body portion shown in FIGS. 1 and 2 and the attached genital-covering panel which forms with the front area of the tubular body portion an accessible pocket.

FIG. 3 is a male undergarment shown generally as 10 which is formed of two basic elements. The first element is a tubular body portion shown generally as 12 in FIG. 1, and the second element is a genital-covering panel shown generally as 14 in FIG. 3. The tubular body portion 12 has a front area 16, a back area 18, and a crotch area 20. The front area has a scrotum-underlying section 22 at its lower edge and an opening 24 defined therein. A waistband 26 encircles the upper perimeter of tubular body portion 12 to encircle securely the waist (or hip, if bikini) of the wearer and hold the garment in a relatively fixed position during use. Tubular body portion 12 can be knit on a circular knitting machine having a selected cylinder diameter and thereby result in a seamless tubular member snugly encircling the torso of the wearer. Where, however, garments are made in varying sizes, it is sometimes necessary to reduce or enlarge the diameter of the seamless tube, thereby resulting in seams 28 such as shown in FIG. 1. Tubular body portion 12 might also be formed from two or more patterns cut for a front area 16 and a back area 18 with seams at 28.

Tubular body portion 12 also includes a pair of leg-receiving openings 30 and is generally patterned while in a generally tubular condition to provide for the formation of the crotch area 20 as shown in FIG. 1 using a single seam 32.

Figure 4:
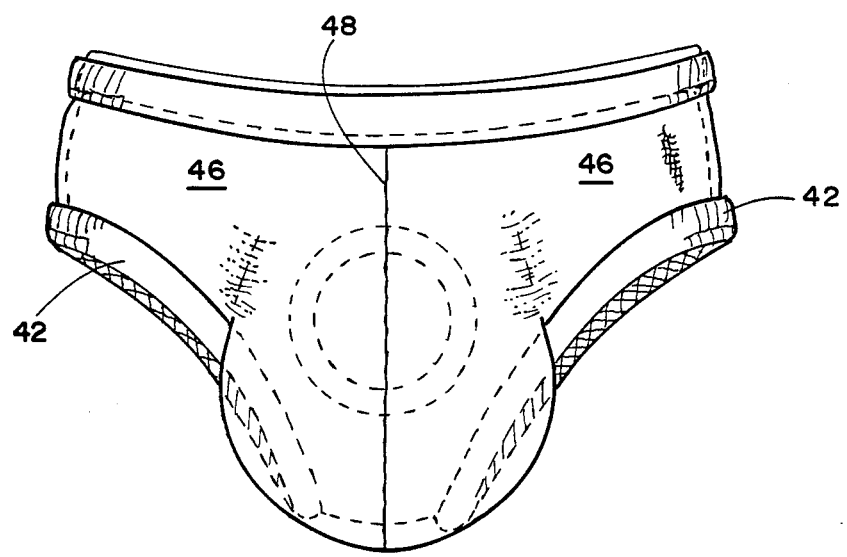
FIG. 4 is a front elevational view of the garment shown in FIG. 3 illustrating the use of two substantially similar sections joined to form the genital-covering panel.

Undergarment 10 is completed by affixing an outer genital-covering panel 14 to the tubular body portion 12 in the manner best shown in FIG. 3. The outer covering panel is shaped to substantially configure with the leg opening and waist border of front area 16 of tubular body portion 12 as is shown in FIG. 4. Genital-covering panel 14 is secured to crotch area 20 of tubular body portion 12 at location 34 which preferably coincides with and becomes seam 32. Genital-covering panel 14 is then connected along the front edges of leg openings 30 to a location 36 which is between the front and back areas 16 and 18 of tubular body portion 12 or would be the side seam if cut from patterns for front and back. If there is a seam 28 in tubular body portion 12, the genital-covering panel becomes connected to the tubular body portion within that seam. The connection continues upwardly to waistband 26.

The upper edge 38 of genital-covering panel portion 14 is provided with stretchable means, preferably a partial waistband, matching that portion used in waistband 26 along back area 18, so that it is held in a substantially contiguous relationship with waistband 26 along front area 16 of tubular body portion 12. Thus the securement of genital-covering panel 14 to tubular body portion 12 at seam 34, along leg openings 30, and upwardly along seam 36 forms a pocket 40 between tubular body portion 12 and genital-covering panel 14. Since the partial waistband 38 is not secured to waistband 26, the pocket is accessible through the upper front area of the garment.

The securement of the genital-covering panel 14 to tubular body portion 12 along leg openings 30 is best accomplished by the use of leg bands 42 which are comprised of strips of stretchable fabric folded over the joined edges of tubular body portion 12 and genital-covering panel 14. Each of the bands 42 encircles an entire leg opening 30. A similar stretchable banding technique is used around opening 24 which prevents unravelling of the fabric around the defined opening.

It has been found desirable to provide a convex pouch portion 44 in genital-covering panel 14 to ensure freedom of movement and air circulation within pocket 40. This may be accomplished by molding the fabric to create a pouch or if using knit fabric by allowing a proper amount of fullness or utilizing two or more fabric segments to form the desired convexity. It has been found advantageous to utilize two substantially similar pieces 46 joined by a vertical seam 48 along the front of the garment as shown in FIG. 4. Obviously, any number of segments can be configured to achieve the desired convexity in such a construction.

The undergarment of the present invention as described and illustrated will provide greater comfort by moisture absorption and air circulation than conventional forms of briefs now being marketed. The garment minimizes binding, pinching, and especially chafing, and at the same time provides anatomically correct freedom for the male genitals as experienced in boxer shorts, but with the additional concealment (modesty) over and beyond that provided by customary briefs, as this invention will totally encase the male genitalia in a pocket preventing the occasional unexpected exposure when wearing a brief under sports garments with short legs. The penis and scrotum which extend through opening 24 are free and not subject to any constriction or binding and are fully covered and protected within pocket 40. Access to the penis may be obtained by simply lifting or moving the partial band 38 downwardly. The retractability of partial band 38 will cause the outer genital-covering panel to return to its initial covering and support position.

The garment of the present invention may be made entirely of a light mesh knit or woven fabric or parts of the garment may be of knit fabric and other parts of woven fabric. The brief may also be made in a variety of sizes resulting from variations in the sizes of the various elements including the tubular support body portion 12, the genital-covering panel 14, and the defined opening 24.

As this invention may be reflected in several forms without departing from its essential characteristics, the present embodiment is, therefore, illustrative and not restrictive, the scope of the invention being defined by the appended claims rather than by the description preceding them. All modifications to the present embodiment that fall within the metes and bounds of these claims or result in alternative embodiments or their functional and cooperative equivalents are intended to be embraced by these claims.

It is claimed:

1. A male undergarment comprising: a tubular body-encasing portion having front, back, and crotch areas and a pair of leg-receiving openings therein, said front area having a scrotum-underlying section and a substantially circular opening defined in said section through which the penis and scrotum are received; a waistband secured to said front area of said tubular body-encasing portion separate from said substantially circular opening; an outer front covering panel having a crotch area connecting edge and an upper edge secured to and extending from said crotch area over said front area proximate said waistband and extending horizontally substantially across said front area to cover more than one-half the circumference of the wearer, said front covering panel being secured to said crotch area along said crotch area connecting edge and extending therefrom along said leg openings to a location between said front and back areas and then upwardly therefrom proximate said waistband thereby forming a separate layer of fabric extending across more than one-half the circumference of the wearer and a genital-receiving pocket between said front area and said front covering panel; stretchable means retaining said upper edge of said front covering panel in a first unsecured contiguous relationship with said waistband and permitting biased displacement of said upper edge of said front covering panel to allow access to said pocket whereby the wearer is provided with an absorbent fabric layer functioning also to protect from rashes and reduce scrotal temperature.

2. The undergarment as claimed in claim 1 whereby said stretchable means is a partial second waistband.

3. The undergarment as claimed in claim 1 whereby said front-covering panel has a convex pouch portion.

4. The undergarment as claimed in claim 1 whereby said front-covering panel has a plurality of joined sections.

5. The undergarment as claimed in claim 1 whereby said joined front-covering panel and each of said leg openings is connected and finished by a stretchable leg band encircling each leg opening.

6. The undergarment as claimed in claim 2 whereby said front-covering panel has a convex pouch portion.

7. The undergarment as claimed in claim 2 whereby said front-covering panel has a plurality of joined sections.

8. The undergarment as claimed in claim 2 whereby said joined front-covering panel and each of said leg openings are connected and finished by a stretchable leg band encircling each leg opening.

9. The undergarment as claimed in claim 3 whereby said front-covering panel has a plurality of joined sections.

10. The undergarment as claimed in claim 3 whereby said joined front-covering panel and each of said leg openings are connected and finished by a stretchable leg band encircling each leg opening.

11. The undergarment as claimed in claim 4 whereby said joined front-covering panel and each of said leg opening are connected and finished by a stretchable leg band encircling each leg opening.

12. The undergarment as claimed in claim 3 whereby said front-covering panel has two substantially similar joined sections.

13. The undergarment as claimed in claim 9 whereby said joined front-covering panel and each of said leg openings are connected and finished by a stretchable leg band encircling each leg opening.

14. The undergarment as claimed in claim 9 whereby said front-covering panel has two substantially similar joined sections.

* * * * *